United States Patent
Edulji et al.

(10) Patent No.: US 10,414,708 B2
(45) Date of Patent: Sep. 17, 2019

(54) METHOD FOR THE PRODUCTION OF GLYCOLS FROM SORBITOL

(71) Applicant: SHELL OIL COMPANY, Houston, TX (US)

(72) Inventors: Smita Edulji, Houston, TX (US); Brendan Dermot Murray, Houston, TX (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 16/319,960

(22) PCT Filed: Jul. 25, 2017

(86) PCT No.: PCT/US2017/043583
§ 371 (c)(1),
(2) Date: Jan. 23, 2019

(87) PCT Pub. No.: WO2018/022538
PCT Pub. Date: Feb. 1, 2018

(65) Prior Publication Data
US 2019/0225565 A1 Jul. 25, 2019

Related U.S. Application Data

(60) Provisional application No. 62/367,384, filed on Jul. 27, 2016.

(51) Int. Cl.
*C07C 29/60* (2006.01)
*C07C 31/20* (2006.01)
*B01J 23/83* (2006.01)

(52) U.S. Cl.
CPC .............. *C07C 29/60* (2013.01); *B01J 23/83* (2013.01); *C07C 31/202* (2013.01); *C07C 31/205* (2013.01)

(58) Field of Classification Search
CPC ..... C07C 29/60; C07C 31/205; C07C 31/202; B01J 23/83
See application file for complete search history.

(56) References Cited

U.S. PATENT DOCUMENTS

| | | |
|---|---|---|
| 5,463,143 A | 10/1995 | Singleton et al. |
| 5,475,159 A | 12/1995 | Singleton et al. |
| 5,475,160 A | 12/1995 | Singleton et al. |

OTHER PUBLICATIONS

International Search Report and Written Opinion received for PCT Patent Application No. PCT/US2017/043583, dated Oct. 5, 2017, 8 pages.

Jin et al., "Sorbitol Hydrogenolysis over Hybrid Cu/CaO—Al2O3 Catalysts: Tunable Activity and Selectivity with Solid Base Incorporation", ACS Catalysis, vol. 5, Issue No. 11, Oct. 5, 2015, pp. 6545-6558, XP055406538.

*Primary Examiner* — Jafar F Parsa

(57) ABSTRACT

Implementations of the disclosed subject matter provide a process for producing ethylene glycol and propylene glycol from a sorbitol feed which may include contacting the sorbitol feed with hydrogen in a reactor in the presence of a solvent and a bi-functional catalyst system. The bi-functional catalyst system may include a first catalyst comprising a copper compound, a zinc compound, and an additional metal compound and a second catalyst comprising sodium carbonate.

10 Claims, 1 Drawing Sheet

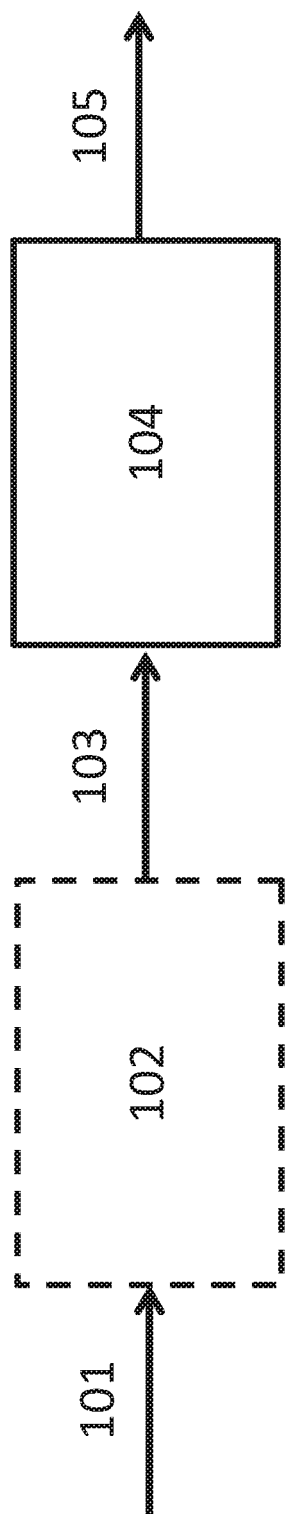

METHOD FOR THE PRODUCTION OF GLYCOLS FROM SORBITOL

CROSS REFERENCE TO RELATED APPLICATIONS

This is a national stage application of International Application No. PCT/US2017/043583, filed 25 Jul. 2017, which claims benefit of priority to U.S. Provisional Application No. 62/367,384, filed 27 Jul. 2016.

CROSS-REFERENCE TO RELATED APPLICATIONS

This application claims priority to U.S. Provisional Application Ser. No. 62/367,384 filed Jul. 27, 2016, the entire disclosure of which is hereby incorporated by reference.

TECHNICAL FIELD OF THE INVENTION

The presently disclosed subject matter relates to a process for converting sorbitol into glycols. More specifically the presently disclosed subject matter relates to a process for preparing glycols, particularly ethylene glycol and propylene glycol, by converting a sorbitol feed material in a reactor using a bi-functional catalyst system.

BACKGROUND

Glycols such as ethylene glycol and propylene glycol are valuable materials with a multitude of commercial applications, e.g. as heat transfer media, antifreeze, and precursors to polymers, such as PET. The market for ethylene and propylene glycols (EG and PG) is expanding worldwide, with the EG market being vastly bigger than the market for PG (i.e., 1,2-propylene glycol). Ethylene and propylene glycols are typically made on an industrial scale by hydrolysis of the corresponding alkylene oxides, which are the oxidation products of ethylene and propylene, produced from fossil fuels/petrochemical feed stocks involving multiple processing steps. Use of bio-based feed stocks for the production of energy and chemicals has become increasingly desirable in the industry since this approach to use feeds from renewable sources provides a pathway for sustainable development.

In recent years, increased efforts have focused on producing chemicals, including glycols, from renewable feedstocks, such as carbohydrate-containing feedstock. Carbohydrates are plentiful and renewable bio-mass feeds, and have the structural features resembling that of ethylene glycol; each carbon has one attached hydroxyl group or contains an oxygen function that can be readily converted into a hydroxyl. As such, EG and PG can be produced if the C—C bonds are selectively cleaved into $C_2$ and $C_3$ units.

As with many chemical processes, the reaction product stream in these processes comprises a number of desired materials as well as diluents, by-products and other undesirable materials. During the hydrogenolysis of glucose and glucose-containing molecules, to form EG and PG, some of the glucose is hydrogenated to sorbitol. Sorbitol cannot undergo retro-aldol conversion to form EG and PG in the hydrogenolysis reaction. As a result sorbitol is a side product and decreases the overall yield of the higher valued EG and PG. In order to provide a high value process, the desirable product or products must be obtainable from the reaction product stream in high purity with a high percentage recovery of each product and with as low as possible use of energy, chemical components and complex equipment.

Therefore, it would be advantageous to provide an improved method suitable for the production of glycols from the by-product, sorbitol, in order to make the overall glycol production process more economical than processes disclosed previously in the industry.

BRIEF SUMMARY

According to an embodiment of the disclosed subject matter, a process for producing ethylene glycol and propylene glycol from a sorbitol feed may include contacting the sorbitol feed with hydrogen in a reactor in the presence of a solvent and a bi-functional catalyst system. The bi-functional catalyst system may include a first catalyst comprising a copper compound, a zinc compound, and an additional metal compound and a second catalyst comprising sodium carbonate.

Implementations of the disclosed subject matter provide an improved method for producing ethylene glycol (EG) and propylene glycol (PG) from sorbitol. The disclosed subject matter allows the desirable products of EG and PG to be obtained from the reaction product stream in high purity with a high percentage recovery of each product and with relatively low use of energy, chemical components and complex equipment as compared to prior processes. This method results in a production of glycols from sorbitol that makes the overall glycol production process more economical than processes disclosed previously in the industry. Additional features, advantages, and embodiments of the disclosed subject matter may be set forth or apparent from consideration of the following detailed description, drawings, and claims. Moreover, it is to be understood that both the foregoing summary and the following detailed description are examples and are intended to provide further explanation without limiting the scope of the claims.

BRIEF DESCRIPTION OF THE DRAWINGS

The accompanying drawing, which are included to provide a further understanding of the disclosed subject matter, are incorporated in and constitute a part of this specification. The drawing also illustrates an embodiment of the disclosed subject matter and together with the detailed description serve to explain the principles of embodiments of the disclosed subject matter. No attempt is made to show structural details in more detail than may be necessary for a fundamental understanding of the disclosed subject matter and various ways in which it may be practiced.

FIG. 1 shows an example process scheme according to an implementation of the disclosed subject matter.

DETAILED DESCRIPTION

Carbohydrates are readily available and renewable bio-mass feeds, and they have the structural features resembling that of ethylene glycol; each carbon has one attached hydroxyl group or contains an oxygen function that can be readily converted into a hydroxyl. Ethylene glycol (EG) and propylene glycol (PG) can be produced by selectively cleaving the C—C bonds into $C_2$ and $C_3$ units. However, during the hydrogenolysis of glucose and glucose-containing molecules, to form EG and PG, some of the glucose is hydrogenated to sorbitol. Sorbitol cannot undergo retro-aldol conversion to form EG and PG in the hydrogenolysis reaction. As a result sorbitol is a side product and decreases the overall yield of higher valued EG and PG. As such, the presently disclosed subject matter relates to a process for preparing glycols, particularly ethylene glycol and propylene glycol, by converting a sorbitol feed material in a reactor using a bi-functional catalyst system.

The hydrogenolysis process variables have major impacts on the conversion and selectivity of the reaction. For example, the particular catalyst(s) used and process conditions can provide for a successful reaction selectivity outcome under a set of practical reaction conditions. Examples of process variables include feed stock (e.g., sucrose, glucose, sorbitol, $C_5$ versus $C_6$ sugars, starch, and the like); one or more catalysts (e.g., having retro-Aldol and hydrogenation functions); temperature, $H_2$ partial pressure, $H_2$/feed ratio, residence time, reaction medium (e.g., a solvent such as water), pH in the reaction medium, and feed/solvent ratio. According to the presently disclosed subject matter, these process variables are identified as being important taking into consideration the chemistry of the reaction discussed below.

The sugars to glycols hydrogenolysis reaction, which is carried out using a metal catalyst and in the presence of hydrogen, is a complex reaction known to produce many products. Since ethylene and propylene glycols are the desired products, the other products must be minimized by selecting the appropriate catalyst and conditions; additionally an EG/PG wt % ratio of at least 1:1 and preferably 7:1 or more is desirable. In general, sugars tend to cleave into $C_3$ fragments more easily than the desired $C_2$ fragment, resulting in the formation of propylene glycol as the single most predominant molecule. However, quite a number of other reactions take place in solution and these side reactions must also be considered. These undesirable side reactions could become dominant particularly under high temperature conditions. As such, in order to maximize production of the desired products EG and PG, it is desirable to convert the by-product material, sorbitol, to ethylene glycol and propylene glycol thereby increasing the yield of these desired products. Multiple equations can be used to explain the various steps of the chemistry of the conversion of sugars to EG and PG, as shown below.

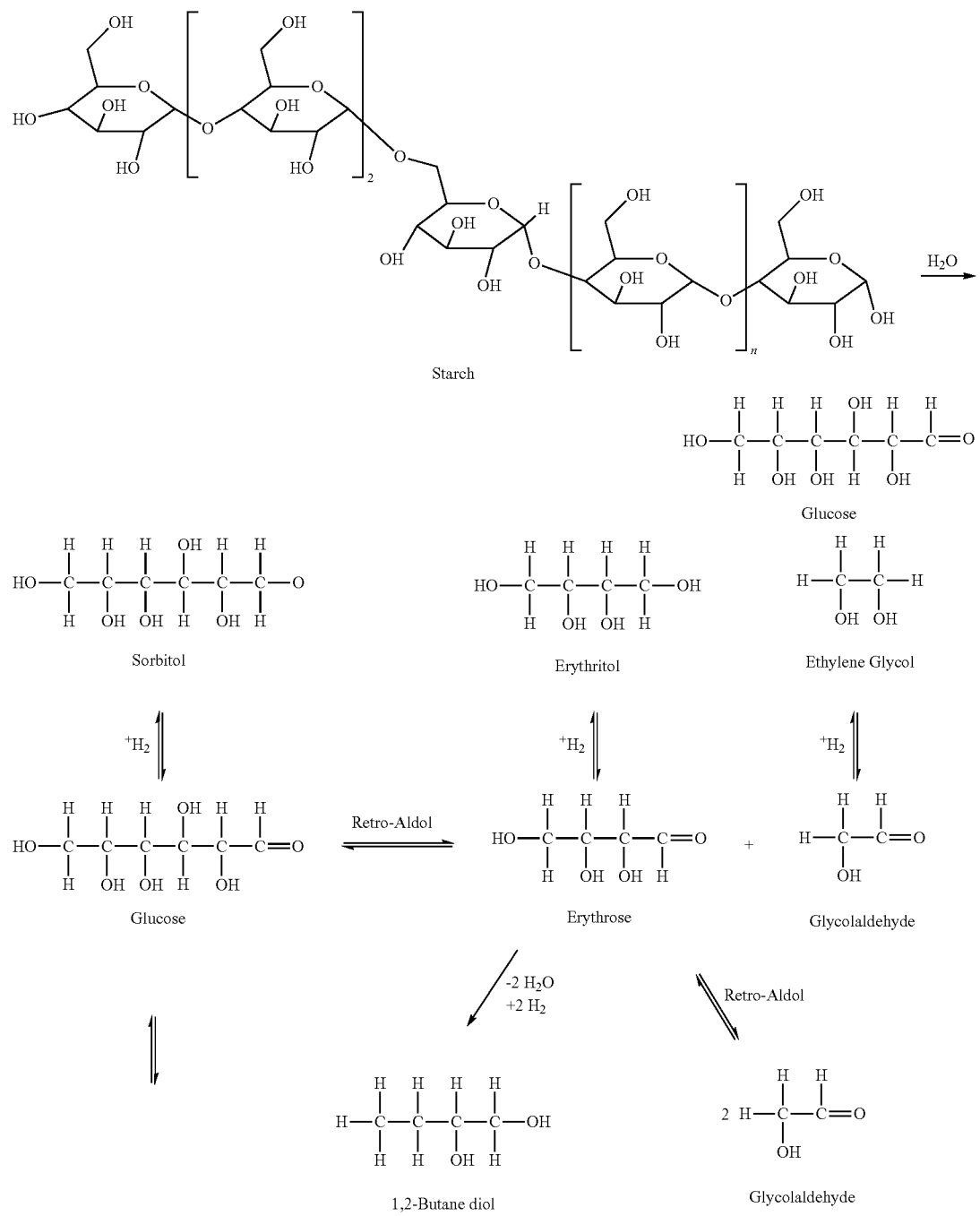

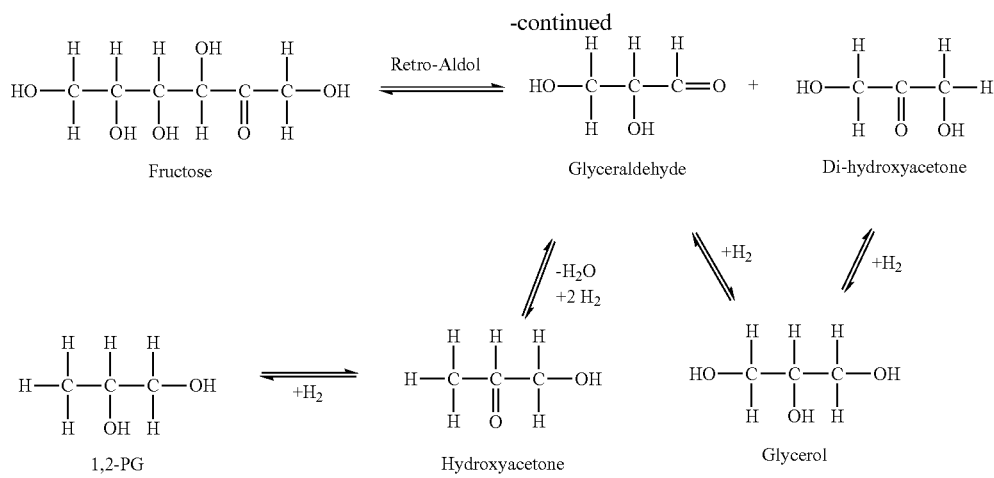

As shown above, the chemistry of sugars in the hydrogenolysis reaction is a notoriously complex set of functional group chemistries; the products from any reaction could be reactants for all other reactions, including those taking place on the surface of the solid catalyst. The product distribution (EG, PG, partially converted sugars, etc.) at the end of reaction will be a function of the relative rates of these reactions under the chosen experimental conditions. Thus, according to the presently disclosed subject matter, a process is provided for preparing glycols, particularly ethylene glycol and propylene glycol, by converting a sorbitol feed material in a reactor using a bi-functional catalyst system.

An advantage of the presently disclosed subject matter is the ability to convert low value sorbitol into higher valued EG and PG. This disclosed process allows for the development of a "greener" route to EG and PG. This bio-based route offers a number of advantages over current EG/PG production based on light olefins. Higher yield "greener" routes to PG and EG may utilize glucose derived via hydrolysis from abundant cellulose. The ability to make EG and PG from a variety of abundant, low cost feedstocks will permit greater process flexibility and more options to improve production.

According to an implementation of the disclosed subject matter, a process for producing ethylene glycol and propylene glycol from a sorbitol feed which may include contacting the sorbitol feed with hydrogen in a reactor in the presence of a solvent and a bi-functional catalyst system. The bi-functional catalyst system may include a first catalyst comprising a copper compound, a zinc compound, and an additional metal compound and a second catalyst comprising sodium carbonate. According to an embodiment, the sorbitol feed may be the product of a hydrogenation process of a C6 monomer containing carbohydrate feed. For example, the C6 monomer containing carbohydrate feed may include one or more of glucose, fructose, sucrose, sugar cane molasses, starch, cellulose, dextrose, and mixtures thereof. In an embodiment, a polymeric feed may be hydrolyzed first into the monomer or oligomers and subsequently hydrogenated to form sorbitol or sorbitol-containing oligomers, or the polymeric feed could be hydrogenated as a sorbitol-containing polymer and subsequently cleaved according to the presently disclosed process. In an embodiment, the concentration of sorbitol in the sorbitol feed may be between about 1 wt % to 75 wt % sorbitol and between about 1 wt % to 50 wt %.

The solvent may be water, a $C_1$ to $C_6$ alcohol, a $C_1$ to $C_6$ polyol, ethers and other suitable organic compounds or mixtures thereof. Further solvent may also be added to the reactor in a separate feed stream or may be added to the sorbitol feed before it enters the reactor. Examples of $C_1$ to $C_6$ alcohols and polyols include methanol, ethanol, 1-propanol, 1,2-hexanediol, glycerol, etc. As an example, the solvent may be a mixture including water and at least one of alcohols, ethers, and ether-alcohols, and mixtures thereof. In an embodiment, the solvent may be water.

Suitable reactor vessels to be used in the process of the preparation of ethylene glycol from a carbohydrate feed include continuous stirred tank reactors (CSTR), plug-flow reactors, slurry reactors, ebullated bed reactors, jet flow reactors, mechanically agitated reactors, back-mixed reactors, bubble columns, such as slurry bubble columns, batch reactor and external recycle loop reactors. The use of these reactor vessels allows dilution of the reaction mixture to an extent that provides high degrees of selectivity to the desired glycol product (mainly ethylene and propylene glycols). There may be one or more of such reactor vessels, arranged in series.

The presently disclosed process may be carried out as a batch process or as a continuous process. In embodiments of the invention wherein the process is a batch process, after addition of all of the portions of the starting material, the reaction may then be allowed to proceed to completion for a further period of time. The reaction product will then be removed from the reactor. In embodiments of the invention wherein the process is carried out as a continuous flow process, after initial loading of some or all of the catalysts and, optionally, solvent, the reactor is heated and pressurized with hydrogen and then the first portion of starting material is introduced into the reactor. Further portions of starting material are then provided to the reactor. Reaction product is removed from the reactor in a continuous manner. In some embodiments of the invention, catalysts may be added in a continuous fashion.

The disclosed method for producing ethylene glycol and propylene glycol from a sorbitol feed may be performed under particular process conditions in order to maximize the desired yield of EG and PG. For example, the process conditions may include temperature, pressure, flow rate, and any other process variable that may be controlled. In an embodiment, the process conditions may include a temperature in the range of from 210-250° C. The hydrogenation conditions may also include a pressure in the range of from 1200 to 3000 psig, and in an embodiment, from 2000 to 2400 psig.

In an embodiment, the presently disclosed method may also include contacting the sorbitol feed with hydrogen. For example, the disclosed method may take place in the presence of hydrogen. Hydrogen may be supplied into the reactor vessel under pressure in a manner common in the art. In an example, the method of the present reaction takes place in the absence of air or oxygen. In order to achieve this, it is preferable that the atmosphere in the reactor vessel be evacuated and replaced with hydrogen repeatedly, after loading of any initial reactor vessel contents, before the reaction starts.

According to an embodiment, the bi-functional catalyst system may include a first catalyst including a copper compound, a zinc compound, and an additional metal compound, and a second catalyst including sodium carbonate.

In an embodiment, the first catalyst may comprise a copper compound, a zinc compound, and an additional metal compound. Examples of this first catalyst may be found in U.S. Pat. Nos. 5,463,143, 5,475,159, and 5,475,160.

The first catalyst may have a copper content in the range of from about 10 wt % to about 70 wt % basis the total weight of the catalyst, from about 25 wt % to about 70 wt % basis the total weight of the catalyst, and from about 30 wt % to about 70 wt % basis the total weight of the catalyst. The Cu based catalysts of the presently disclosed subject matter achieve a high degree of sorbitol cracking to yield more EG and PG. Other catalyst systems are known for the conversion of sorbitol to EG and PG. For example, Ni or many Ni complexes may be used in a sorbitol cracking catalyst, however these are often associated with health, safety, and environmental issues. The new copper based complexes according to the presently disclosed subject matter offer advantages over other catalysts, such as Ni catalysts, in that they exhibit high sorbitol cracking without the known toxicological issues of nickel containing catalysts.

The first catalyst may also have a zinc content in the range of from about 10 wt % to about 65 wt % basis the total weight of the catalyst, from about 15 wt % to about 60 wt % basis the total weight of the catalyst, and from about 20 wt % to about 60 wt % basis the total weight of the catalyst.

Additionally, the first catalyst may have an additional metal compound content in the range of from about 0.1 wt % to about 20 wt % basis the total weight of the catalyst, from about 0.2 wt % to about 15 wt % basis the total weight of the catalyst, and from about 0.3 wt % to about 10 wt % basis the total weight of the catalyst. In particular, the additional metal compound may be one or more of zirconium, aluminum, magnesium, praseodymium, neodymium, promethium, gadolinium, yttrium, lanthanum, samarium, thorium, cerium, europium, terbium, dysprosium, holmium, erbium, thulium, ytterbium, lutetium, titanium, scandium, and mixtures thereof. In an example, the additional metal compound may be lanthanum. In this case, the first catalyst may further include at least one metal selected from zirconium, aluminum, magnesium, praseodymium, neodymium, promethium, gadolinium, yttrium, samarium, thorium, cerium, europium, terbium, dysprosium, holmium, erbium, thulium, ytterbium, lutetium, titanium, scandium, and mixtures thereof.

The second catalyst may include sodium carbonate. In the sorbitol cracking processes of the prior art, La(OH)$_3$ was used as a co-catalyst. However, according to the presently disclosed subject matter, the second catalyst, or co-catalyst, includes Na$_2$CO$_3$ which is a less expensive alternative as compared to La(OH)$_3$ used in the prior art.

Various procedures can be utilized to prepare the catalysts of the present invention (e.g., U.S. Pat. Nos. 5,463,143, 5,475,159, and 5,475,160). For example, individual solutions of the metals may be prepared and mixed together followed by the addition of an aqueous alkaline solution. Alternatively, a first aqueous solution comprising a copper or zinc salt and a second solution comprising a soluble base and at least one soluble salt of at least one second metal can be prepared, and these two solutions are then added simultaneously to a vessel containing water. In a preferred embodiment, the catalysts are prepared by co-precipitating from aqueous solution thermally decomposable compounds of copper, zinc, and at least one additional metal compound, washing the precipitate and calcining the precipitate to give the metal oxides. The catalyst precursor is subjected to a reduction treatment to give the active catalyst.

It is understood that the catalyst is usually handled and stored in the form of its precursor, which indeed is referred to in commerce as the "catalyst", although it is not the catalyst in the strict sense of the agent taking part in chemical reactions such as conversion of sorbitol to EG and PG. Reduction of the precursor to the catalyst is normally carried out by the operator of the chemical process. The precursor may be in shapes, e.g., pellets, as required by the user of the catalyst, or may be in its condition before the shaping operation, e.g., as powder or lightly compressed powder. The initial form in which the copper, zinc and at least one additional metal compound are employed is the oxide, although compounds which are readily converted to the oxide, e.g., the corresponding metal carbonates, are also suitable initially employed as these are converted to the oxide during pretreatment subsequent to the formation of the initially prepared catalyst composition.

Pretreatment of the catalyst in hydrogen and operation of the catalyst in the reaction environment will cause at least partial reduction of some of the metals, such as copper, to lower oxidation states, and it is intended that catalysts with these reduced states will fall within the scope of the presently disclosed subject matter.

According to an embodiment, when the concentration of sorbitol in the sorbitol feed is between about 1 wt % to 75 wt % sorbitol, the ratio of the amount of the first catalyst to the second catalyst is between about 0.3 to 1. As a specific example, the ratio of the amount of the first catalyst to the second catalyst is about 0.3 to 1 produced high yields with a 1 wt % sorbitol feed in a batch reactor. In an embodiment, the total amount of the first and second catalysts may be 0.3-0.5 wt % on the basis of the total reactants and solvent entering the reactor.

According to an embodiment, any active catalyst component may be present in either heterogeneous or homogeneous form. In this case, any active catalyst component may be supported on a solid support.

The solid support may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxides, zirconium hydroxides, magnesium oxides, zinc oxides, titanium oxides, carbons, activated carbons, zeolites, clays, silica aluminas and mixtures thereof.

According to the presently disclosed subject matter, a product stream may be obtained from the reactor. The product stream may include both EG and PG. In particular, the product stream may include a yield of at least 10 wt % EG, and at least 15 wt % EG. In addition, the product stream may include a yield of at least 15 wt % PG, and at least 20 wt % PG.

FIG. 1 shows an example process scheme according to an implementation of the disclosed subject matter. As shown in FIG. 1, a feed 101 may include a C6 monomer containing carbohydrate feed and a solvent and may be provided to a pre-treatment unit 102 to convert it mainly into sorbitol or a sorbitol-containing feed in solvent to form feed 103. The pre-treatment unit 102 may consist of multiple other units. This pre-treatment is an optional step in case the feed does not contain sorbitol. A sorbitol-containing feed 103 may be fed to the main reactor 104 where it may undergo a reaction in the presence of the bi-catalyst system to produce a product stream comprising of EG and PG 105. Although not shown in FIG. 1, reactor 104 may include an agitator (e.g., magnetic stir bars) for mixing the solution. In one example, the first catalyst with water (e.g., a slurry of the catalyst and water) may be pre-loaded in the reactor 104. The first catalyst may be activated by reduction with hydrogen supplied to the reactor 104. Next, the temperature may be increased to the desired reaction temperature. An additional feed line may be used for feeding the second catalyst into reactor 104. In an example, the reactor 104 may be pre-loaded with the first catalyst and the second catalyst may be continuously added to the reactor 104. In one embodiment, the second catalyst may be continuously added to the reactor 104 via the sorbitol feed 103. Two or more of the liquid feeds may be combined into one or more feed lines to the reactor 104. The pressure in reactor 104 may be controlled by a pressure control valve and excess hydrogen may be vented from reactor 104 via an off-gas line (not shown). A level controlling device (not shown) may measure the volume within reactor 104 in order to maintain a constant volume. The product stream 105 may be removed from reactor 104.

As shown in the Examples section provided below, the presently disclosed method for producing ethylene glycol from a carbohydrate feed has numerous advantages over the prior art. The disclosed method provides for various process conditions that, when combined, achieve superior results in terms of product yield, catalyst stability, and extended run time (e.g., suitable for commercialization). The presently disclosed method allows for the use of a carbohydrate feed with a high carbohydrate concentration, superior results and advantages over the prior art are achieved. As a result, the presently disclosed method has the advantages of achieving high total glycol yield (i.e., EG, PG).

EXAMPLES

For the experiments, 75 ml Hastelloy C batch autoclaves, with magnetic stir bars were used. In typical experiments, known weights of catalysts and feed were added to the autoclaves along with 30 ml of the solvent (typically water). If the catalysts or feedstocks were present as slurries or solutions, the total volume of those as well as the solvent was kept at 30 ml.

Example 1

In Example 1, 0.3 g of sorbitol and known weights of catalysts were added to 30 ml of water. The loaded autoclave was then purged three times with nitrogen, followed by hydrogen purge. The hydrogen pressure was then raised to 2000 psig or approximately 14 MPa of hydrogen and the autoclave was sealed and left stirring to perform a leak test.

After performing the leak test, the autoclave was de-pressurized to the target hydrogen pressure (1350 psig or 9.41 MPa) at room temperature, and closed. Next the temperature was ramped to the target run temperature of 220° C. as a fast ramp. The autoclave was held at the target temperature for 135 min, while both the temperature and pressure were monitored. After the required run time had elapsed, the heating was stopped, and the reactor was cooled down to room temperature, de-pressurized, purged with nitrogen and then opened.

The contents of the autoclave were then analyzed via Gas Chromatography (GC) or High Pressure Liquid Chromatography (HPLC) after being filtered.

Table 1 provides details on the catalyst systems tested in Example 1. Catalyst system A is comparative in nature. Catalyst system B is according to the presently disclosed subject matter.

TABLE 1

| Catalyst System | Catalyst 1 | Catalyst 1 Amount, g | Catalyst 2 | Catalyst 2 Amount, g |
| --- | --- | --- | --- | --- |
| A | None | — | Cu/Zn/La oxides | 0.15 |
| B | Sodium carbonate | 0.15 | Cu/Zn/La oxides | 0.15 |

The results of example 1 are provided in Table 2 below.

TABLE 2

| Catalyst System | EG, wt % | PG, wt % | Glycerol, wt % |
| --- | --- | --- | --- |
| A | 5.8 | 6.9 | 6.8 |
| B | 12.2 | 23.6 | 11.6 |

It is apparent from Table 2 that the sodium carbonate co-catalyst, as described in the presently disclosed subject matter, is necessary to achieve higher yields of glycols (i.e., 12.2 wt % EG and 23.6 wt % PG) as compared to the results (i.e., 5.8 wt % EG and 6.9 wt % PG) when the sodium carbonate co-catalyst is not used. This example shows that without the sodium carbonate co-catalyst (as in comparative catalyst system A) the combined EG+PG yield is 12.7 wt %, while in the presence of sodium carbonate (as in catalyst system B according to the presently disclosed subject matter) the combined EG+PG yield is 35.8 wt %, which is significantly higher. The Cu/Zn/La oxide catalyst alone is not sufficient to achieve higher yields of glycols. As shown, according to the presently disclosed subject matter, sodium carbonate co-catalyst has a synergistic effect and is necessary in addition to the Cu/Zn/La oxide catalyst.

Example 2

The same methodology as described in Example 1 was used for Example 2. The catalyst systems used in Example 2 are described in Table 3. Catalyst systems C and E are comparative examples. Catalyst systems D and F are according to the presently disclosed subject matter.

TABLE 3

| Catalyst System | Catalyst 1 | Catalyst 1 Amount, g | Catalyst 2 | Catalyst 2 Amount, g |
|---|---|---|---|---|
| C | Sodium carbonate | 0.05 | Copper chromite catalyst | 0.075 |
| D | Sodium carbonate | 0.05 | Cu/Zn/La oxides | 0.075 |
| E | Sodium carbonate | 0.025 | Copper oxide 5-15 wt. %/ activated carbon (Sud Chemie C8-7) | 0.075 |
| F | Sodium carbonate | 0.025 | Cu/Zn/La oxides | 0.075 |

The results of example 2 are provided in Table 4.

TABLE 4

| Catalyst System | EG, wt % | PG, wt % | Glycerol, wt % |
|---|---|---|---|
| C | 0.0 | 2.5 | 0.0 |
| D | 16.6 | 28.4 | 24.1 |
| E | 0.0 | 1.5 | 0.0 |
| F | 13.4 | 22.4 | 15.9 |

It is apparent from Table 4 that using only a copper-based catalyst with a sodium carbonate co-catalyst was not sufficient to achieve high glycol yields and that the catalyst system of the presently disclosed subject matter is necessary to achieve high yields of glycols. In examples C and E copper chromite and copper oxide on a carbon support were used as the copper-containing catalysts, respectively, along with the sodium carbonate. In both examples C and E, the combined glycol yields (EG+PG) were fairly negligible (<3 wt %). However, when Zn and La compounds were added to copper oxide to form the presently disclosed copper-containing catalyst in examples D and F, significantly higher glycol yields of 45 wt % and 35.8 wt %, respectively, were obtained. This clearly shows that copper-only based catalysts with sodium bicarbonate co-catalyst (i.e., comparative example catalyst systems C and E) were not sufficient to achieve high yields of glycols as compared the catalyst system (i.e., catalyst systems D and F) of the presently disclosed subject matter.

Example 3

The same methodology as described in Example 1 was used for Example 3. The catalyst systems used in Example 3 are described in Table 5. Catalyst systems G through M are comparative examples. Catalyst system F is according to the presently disclosed subject matter.

TABLE 5

| Catalyst System | Catalyst 1 | Catalyst 1 Amount, g | Catalyst 2 | Catalyst 2 Amount, g |
|---|---|---|---|---|
| G | Sodium carbonate | 0.025 | CuO 41%, Cr2O3 43%, BaO 12% (Sud Chemie G22) | 0.075 |
| H | Sodium carbonate | 0.025 | CuO 78%, Cr2O3 20%, contains barium compounds < 0.5 wt. % (Sud Chemie T-4419) | 0.075 |
| I | Sodium carbonate | 0.025 | CuO 47%, Cr2O3 34%, BaO 6% Balance SiO2 (Sud Chemie G22/2) | 0.075 |
| J | Sodium carbonate | 0.025 | CuO 47%, Cr2O3 46%, MnO2 4%; BaO 2% (Sud Chemie G99) | 0.075 |
| K | Sodium carbonate | 0.025 | Carulite 200 - MnO2 60-75%/ CuO 11-14%/ AlO 8-18% | 0.075 |
| L | Sodium carbonate | 0.025 | CuO 56%, MnO2 < 10%, Al2O3 balance (Sud Chemie T-4489) | 0.075 |
| M | Sodium carbonate | 0.025 | CuO; ZnO; Mn oxides < 10% (Sud Chemie T-4492) | 0.075 |
| F | Sodium carbonate | 0.025 | Cu/Zn/La oxides | 0.075 |

The results of Example 3 are provided in Table 6 below.

TABLE 6

| Catalyst System | EG, wt % | PG, wt % | Glycerol, wt % |
|---|---|---|---|
| G | 0.0 | 0.0 | 0.0 |
| H | 3.6 | 2.0 | 0.0 |
| I | 0.0 | 0.0 | 0.0 |
| J | 3.2 | 1.6 | 0.0 |
| K | 0.0 | 1.1 | 0.0 |
| L | 4.7 | 5.1 | 1.3 |
| M | 4.0 | 3.6 | 1.4 |
| F | 13.4 | 22.4 | 15.9 |

It is apparent from Table 6 that using only copper-based tri- and quad-metallic catalysts with a sodium carbonate co-catalyst was not sufficient to achieve high glycol yields as compared to the bi-functional catalyst system of the presently disclosed subject matter. Further, as shown in Table 6, the catalyst system of the presently disclosed subject matter is necessary to achieve a higher yield of glycols. A variety of different tri- and quad-metallic copper-based catalysts were tested in comparative examples G-M such as Cu/Cr/Ba, Cu/Cr/Ba/Mn, Cu/Cr/Mn, and Cu/Mn/Al systems, along with sodium carbonate. All of the comparative examples G-M resulted in low combined glycol yields relative to the yields achieved by the presently disclosed bi-functional catalyst system. Even when Cu/Zn/Mn system (catalyst system M) was used it did not result in the high glycol yields of 35.8 wt % which were achieved when the $3^{rd}$ component was La and not Mn. This indicates that very specific catalyst compositions of Cu—Zn catalysts as defined in the presently disclosed subject matter are effective catalysts to achieve high combined glycol yields and not all Cu-based or Cu—Zn-based tri- and quad-metallic systems are able to achieve these high combined glycol yields.

Example 4

This example shows the optimization of the amount of catalyst needed. The same methodology as described in Example 1 was used for Example 4. The catalyst systems used in Example 4 are described in Table 7. Catalyst systems D, F, and N through S are examples comparing varying amounts of each of the catalysts 1 and 2 and comparing varying ratios of catalyst 1 to catalyst 2.

TABLE 7

| Catalyst System | Catalyst 1 | Catalyst 1 Amount, g | Catalyst 2 | Catalyst 2 Amount, g | Ratio of Catalyst 1:Catalyst 2 | Total Amount of Catalyst, g | Catalyst as % of total reactants and solvent |
|---|---|---|---|---|---|---|---|
| N | Sodium carbonate | 0.017 | Cu/Zn/La oxides | 0.025 | 0.68 | 0.042 | 0.14 |
| O | Sodium carbonate | 0.025 | Cu/Zn/La oxides | 0.025 | 1 | 0.050 | 0.17 |
| P | Sodium carbonate | 0.05 | Cu/Zn/La oxides | 0.05 | 1 | 0.100 | 0.33 |
| F | Sodium carbonate | 0.025 | Cu/Zn/La oxides | 0.075 | 0.333333 | 0.100 | 0.33 |
| D | Sodium carbonate | 0.05 | Cu/Zn/La oxides | 0.075 | 0.666667 | 0.125 | 0.41 |
| Q | Sodium carbonate | 0.075 | Cu/Zn/La oxides | 0.075 | 1 | 0.150 | 0.50 |
| R | Sodium carbonate | 0.1 | Cu/Zn/La oxides | 0.075 | 1.333333 | 0.175 | 0.58 |
| S | Sodium carbonate | 0.15 | Cu/Zn/La oxides | 0.15 | 1 | 0.300 | 0.99 |

The results of example 4 are provided in Table 8.

TABLE 8

| Catalyst System | EG, wt % | PG, wt % | Glycerol, wt % |
|---|---|---|---|
| N | 8.1 | 12.9 | 5.4 |
| O | 7.5 | 10.5 | 3.3 |
| P | 15.6 | 25.6 | 18.8 |
| F | 13.4 | 22.4 | 15.9 |
| D | 16.6 | 28.4 | 24.1 |
| Q | 12.9 | 21.7 | 15.2 |
| R | 9.5 | 23.6 | 23.3 |
| S | 12.2 | 23.6 | 11.6 |

It is apparent from Table 8 that catalyst system D provides the highest yields of glycols. When the ratio and loading of the total amount of catalysts is varied it is apparent that it is not only the ratio of the two catalysts that is important but also the total amount of catalysts that is loaded relative to the reactants and solvent amount. Based on the results provided in Table 8, it is apparent that high combined glycol yields are obtained when the ratio of Catalyst 1 to Catalyst 2 is in the range of 0.3-1, while the total catalyst loading may be be 0.3-0.5 wt % of the reactants and solvent stream.

Example 5

The same methodology as described in Example 1 was used for Example 5. The catalyst systems used in Example 5 are described in Table 9. Catalyst systems T, U, and W are comparative examples, while catalyst system D is according to the presently disclosed subject matter.

TABLE 9

| Catalyst System | Catalyst 1 | Catalyst 1 Amount, g | Catalyst 2 | Catalyst 2 Amount, g |
|---|---|---|---|---|
| T | Lanthanum (III) hydroxide | 0.005 | 5% Ni on C | 0.3 |
| U | Lanthanum (III) hydroxide | 0.005 | Raney Ni 2400 promoted by Fe and Cr | 0.022 |
| W | Sodium carbonate | 0.025 | Raney Ni 2800 | 0.021 |

TABLE 9-continued

| Catalyst System | Catalyst 1 | Catalyst 1 Amount, g | Catalyst 2 | Catalyst 2 Amount, g |
|---|---|---|---|---|
| D | Sodium carbonate | 0.05 | Cu/Zn/La oxides | 0.075 |

The results of Example 5 are provided in Table 10.

TABLE 10

| Catalyst System | EG, wt % | PG, wt % | Glycerol, wt % |
|---|---|---|---|
| T | 7.2 | 9.9 | 14.6 |
| U | 5.5 | 7.1 | 13.7 |
| W | 4.6 | 3.3 | 6.6 |
| D | 16.6 | 28.4 | 24.1 |

In the prior art, various Ni-based catalysts and lanthanum (III) hydroxide catalysts were used for sorbitol cracking experiments. Using comparative catalyst systems T, U, and W as representative catalyst systems described in the prior art, the achieved combined glycol yields were compared with the results achieved by catalyst system D which is according to the presently disclosed subject matter. It is apparent from Table 10 that catalyst system D achieves the highest yields of glycols as compared to the various Ni-based catalysts and lanthanum (III) hydroxide comparative catalyst systems T, U, and W, demonstrating that catalysts system according to the presently disclosed subject matter is a significantly more effective sorbitol cracking system than the ones used in prior art.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

That which is claimed is:

1. A process for producing ethylene glycol and propylene glycol from a sorbitol feed comprising:
    contacting the sorbitol feed with hydrogen in a reactor in the presence of a solvent and a bi-functional catalyst system comprising:
        1) a first catalyst comprising a copper compound, a zinc compound, and an additional metal compound, and
        2) a second catalyst comprising sodium carbonate.

2. The process of claim 1, wherein the additional metal compound comprises at least one selected from the group consisting of: zirconium, aluminum, magnesium, praseodymium, neodymium, promethium, gadolinium, yttrium, lanthanum, samarium, thorium, cerium, europium, terbium, dysprosium, holmium, erbium, thulium, ytterbium, lutetium, titanium, scandium, and mixtures thereof.

3. The process of claim 1, wherein the additional metal compound comprises lanthanum.

4. The process of claim 3, wherein the first catalyst further comprises at least one metal selected from the group consisting of: zirconium, aluminum, magnesium, praseodymium, neodymium, promethium, gadolinium, yttrium, lanthanum, samarium, thorium, cerium, europium, terbium, dysprosium, holmium, erbium, thulium, ytterbium, lutetium, titanium, scandium, and mixtures thereof.

5. The process of claim 1, wherein the concentration of sorbitol in the sorbitol feed is between about 1 wt % to 75 wt % sorbitol.

6. The process of claim 5, wherein the ratio of the amount of the first catalyst to the second catalyst is between about 0.3 to 1.

7. The process of claim 6, wherein the total amount of the first and second catalysts is 0.3-0.5 wt % on the basis of the total reactants and solvent entering the reactor.

8. The process of claim 1, wherein the sorbitol feed is the product of a hydrogenation process of a C6 monomer containing carbohydrate feed.

9. The process of claim 1, further comprising obtaining a product stream from the reactor comprising a yield of at least 10 wt % EG.

10. The process of claim 1, further comprising obtaining a product stream from the reactor comprising a yield of at least 15 wt % PG.

* * * * *